United States Patent
Arnold et al.

(10) Patent No.: US 11,285,482 B2
(45) Date of Patent: Mar. 29, 2022

(54) MOLECULAR SENSING DEVICE

(71) Applicant: LOCKHEED MARTIN CORPORATION, Bethesda, MD (US)

(72) Inventors: Sanipa Koetsawasdi Arnold, Bethesda, MD (US); Madiha Jamil Jafri, Bethesda, MD (US); Paul L. Okun, Bethesda, MD (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 16/137,886

(22) Filed: Sep. 21, 2018

(65) Prior Publication Data
US 2020/0094250 A1     Mar. 26, 2020

(51) Int. Cl.
*B01L 3/00* (2006.01)
*A61B 90/00* (2016.01)
*G01N 29/02* (2006.01)

(52) U.S. Cl.
CPC ........ *B01L 3/502753* (2013.01); *A61B 90/06* (2016.02); *B01L 3/502715* (2013.01); *B01L 3/502784* (2013.01); *G01N 29/022* (2013.01); *A61B 2562/028* (2013.01); *B01L 2300/0627* (2013.01)

(58) Field of Classification Search
CPC .............. A61B 2562/028; A61B 90/06; B01L 2300/0627; B01L 2300/0663; B01L 3/502715; B01L 3/502753; B01L 3/502784; G01N 27/3275; G01N 29/022; G01N 29/222
See application file for complete search history.

(56) References Cited

U.S. PATENT DOCUMENTS

| | | | |
|---|---|---|---|
| 8,125,331 B2 | 2/2012 | Allen et al. | |
| 8,236,243 B2 | 8/2012 | Palena et al. | |
| 9,133,024 B2 | 9/2015 | Phan et al. | |
| 9,277,864 B2 | 3/2016 | Yang et al. | |
| 2004/0045891 A1* | 3/2004 | Gilbert | B01L 3/502738 210/321.65 |
| 2007/0270672 A1 | 11/2007 | Hayter | |

(Continued)

OTHER PUBLICATIONS

Echologics products: "LeakFinder-ST™ Correlator" and "LeakFinder-ST: Advanced Acoustic Leak Detection System" by Echologics, available at https://www.echologics.com/products/leakfinderst/, 6 pages.

*Primary Examiner* — Jennifer Wecker
(74) *Attorney, Agent, or Firm* — Baker Botts L.L.P.

(57) ABSTRACT

A molecular sensing device and method are described that include a microfluidics layer, a transduction layer fluidly connected to the microfluidics layer, and a transceiver layer electro-mechanically connected to the transduction layer. The microfluidics layer is configured to collect a sample from an environment, the transduction layer is configured to detect a presence of a specific analyte within the sample, and the transceiver layer is configured to generate an electrical signal in response to the specific analyte detected by the transduction layer and configured to transmit the electrical signal. At least a portion of the transduction layer and/or at least a portion of the microfluidics layer is configured to be replaceable without replacing a remaining portion of the transduction layer or the microfluidics layer.

20 Claims, 4 Drawing Sheets

(56) References Cited

U.S. PATENT DOCUMENTS

| | | | |
|---|---|---|---|
| 2009/0129728 A1* | 5/2009 | Arnold | B01J 19/0093 |
| | | | 385/52 |
| 2009/0299156 A1 | 12/2009 | Simpson et al. | |
| 2013/0018243 A1* | 1/2013 | Palena | B01L 3/502753 |
| | | | 600/345 |
| 2014/0148670 A1 | 5/2014 | Reggiardo et al. | |

* cited by examiner

MOLECULAR SENSING DEVICE

FIELD

This disclosure relates to a sensing device, in particular a molecular sensing device and methods using the same.

BACKGROUND

There are certain molecules that are associated with harmful health conditions (e.g., diseases) such as cancer. Generally, early treatment of harmful health conditions may provide patients increased treatment options and/or management for such conditions. Early detection of harmful health conditions is a critical component in risk management and/or treatment options.

Currently, while external (in vitro) tests are available for cancer and/or disease detection, the results from the tests require days to weeks of undesirable latency. Many diseases do not have a diagnostic test to detect an early stage of the illness, such as cancer, until it has progressed to later stages and spread beyond the primary stage of the tumor site.

Current noninvasive test methods may be undertaken once to a few times a year. For example, early stage cancer detection methods currently include going through infrequent, periodic screenings that can be time consuming, costly, and may not provide an adequate early warning detection of disease. The current noninvasive test methods (e.g., X-rays, Magnetic Resonance Imaging, Computed Tomography, etc.) fail to detect a high percentage of tumors in the chest cavity and other organs due to high "clutter levels" (i.e., signatures that blend into their surrounding similar to noise and human error).

SUMMARY

Molecular sensing devices and methods are described herein that can be used to monitor and provide early detection of, for example, a contaminant(s) and/or a harmful health condition(s). Embodiments of the molecular sensing devices can provide early detection via persistent external or internal monitoring for one or more specific groups of molecular markers (i.e. one or more analytes) capable of being platform independent at a microscale. The embodiments described herein are directed to molecular sensing devices that include a portion which can be replaced (e.g., "swappable") without replacing other portions/components of the sensing device. The term swappable refers to a component within the molecular sensing device that can be replaced and/or removed (e.g., exchanged), as discussed in further detail herein.

The swappable feature can facilitate reuse of remaining portions of the sensing device thereby reducing waste and increasing the lifespan of the sensing device, while maintaining accurate detection. In some embodiments, the swappable feature can facilitate the detection of multiple and/or different analytes. In other embodiments, a broad variety of contaminant leaks may be monitored to detect analytes that may cause harmful health conditions.

The sensing devices described herein can perform microscale external (in vitro) or internal (in vivo) platform independent persistent monitoring of multiple molecular markers for real-time contaminant or disease detection involving, but not limited to, human or animal organisms as well as non-human and non-animal related detection. The sensing devices described herein can provide an early warning diagnostic system(s) for Chemical, Biological, Radiological and Nuclear (CBRN) commercial and defense industries. For example, the described sensing devices can provide enhanced, sensitive, real-time monitoring systems that can detect contaminant leaks, which may be harmful to biological health, in CBRN industries. Early detection of contaminant leaks is advantageous to minimize risks associated with environmental damage and/or existing structures (e.g., pipelines, HVAC systems, battle grounds, etc.). The described sensing devices can also provide an early warning diagnostic system(s) within an environment having a challenging detection environment, such as within a pipeline having a turbulent flow (e.g. high velocity). The described sensing devices can also be modified by replacing a portion thereof to account for changes in a particular contaminant that may be of concern.

Embodiments of the molecular sensing device described herein can include a microfluidics layer, a transduction layer fluidly connected to the microfluidics layer, and a transceiver layer electro-mechanically connected to the transduction layer. The microfluidics layer is configured to collect a sample from an environment, the transduction layer is configured to detect a presence of an analyte within the sample, and the transceiver layer is configured to generate an electrical signal in response to the analyte detected by the transduction layer and configured to transmit the electrical signal. At least a portion of the transduction layer and/or at least a portion of the microfluidics layer is configured to be replaceable without replacing a remaining portion of the transduction layer or the microfluidics layer.

The transduction layer is positioned between the microfluidics layer and the transceiver layer to form a multi-layered structure. In some embodiments, the transduction layer includes a detector sub-layer and a well sub-layer that includes a plurality of wells, and at least one of the detector sub-layer or the well sub-layer is replaceable. The detector sub-layer includes a first surface and a second surface opposite the first surface. The first surface is releasably secured to a surface of a first sub-layer adjacent to the detector sub-layer. The first surface can be releasably secured to the surface of the first sub-layer adjacent to the detector sub-layer via an adhesive. In some embodiments, the detector sub-layer can be peelable from the sub-layer adjacent to the detector sub-layer.

The well sub-layer includes a first surface and a second surface opposite the first surface. In some embodiments, the first surface is releasably secured to a surface of a first sub-layer adjacent to the well sub-layer, and the second surface is releasably secured to a surface of a second sub-layer adjacent to the well sub-layer.

In some embodiments, each of the detector sub-layer and the well sub-layer are replaceable. Additionally, or alternatively, in some embodiments, the microfluidics layer includes a systems sub-layer that includes a plurality of micro-electro-mechanical systems (MEMS), and the systems sub-layer is replaceable.

The molecular sensing device may provide many benefits related to the detection of contaminants and/or harmful health conditions. For instance, the molecular sensing device can provide persistent surveillance of molecular markers and/or biomarkers associated with contamination and/or disease, thereby providing early detection. The early detection may provide additional time to abate the contaminant and/or acquire treatment for a disease/illness.

Additionally, the molecular sensing device may be discrete and compact. The molecular sensing device can function within a single microscale three dimensional sensor, which can capture, concentrate, direct, detect, identify, measure, and communicate measured values with respect to specific molecular markers associated with targeted contaminants/diseases in real-time. The molecular sensing device can be altered such that a component can be removed and/or replaced (e.g., swapped/exchanged) without altering the remaining components in the sensing device.

DETAILED DESCRIPTION

Molecular sensing devices and methods are described that can provide early detection via persistent external or internal monitoring for one or more specific groups of molecular markers (i.e., one or more analytes) capable of being platform independent at a microscale. The molecular sensing device includes a portion which can be replaced (e.g., "swappable") without replacing other portions/components. As used herein, the term swappable is synonymous with exchange, and refers to a feature that can be removed and/or replaced with another feature or no feature. By way of one non-limiting example, the molecular sensing device can include a detector that may be removed and/or replaced with the same or different detector. The same detector can detect the same molecular marker(s) and/or a different detector a different molecular marker(s).

Embodiments of the sensing device can be used to detect contaminants and/or harmful health conditions. For example, a pipeline transporting oil from one area to another area may be compromised at a location there-between. Oil may escape the pipeline and contaminate a surrounding area. The escaped oil may contaminate the ground, soil, and/or air. The molecular sensing device can detect molecular markers (i.e., analytes) on the ground, in the soil, or in the air that may cause harmful health conductions, such as cancer. The molecular sensing device can measure and determine a concentration of the molecules. The detection of the contamination and/or harmful health condition may provide additional time for abatement of the contaminant and/or treatment for the health condition. In other embodiments, the sensing device can be used within, on or near a human or animal to detect a molecular marker of interest.

Figure 1:
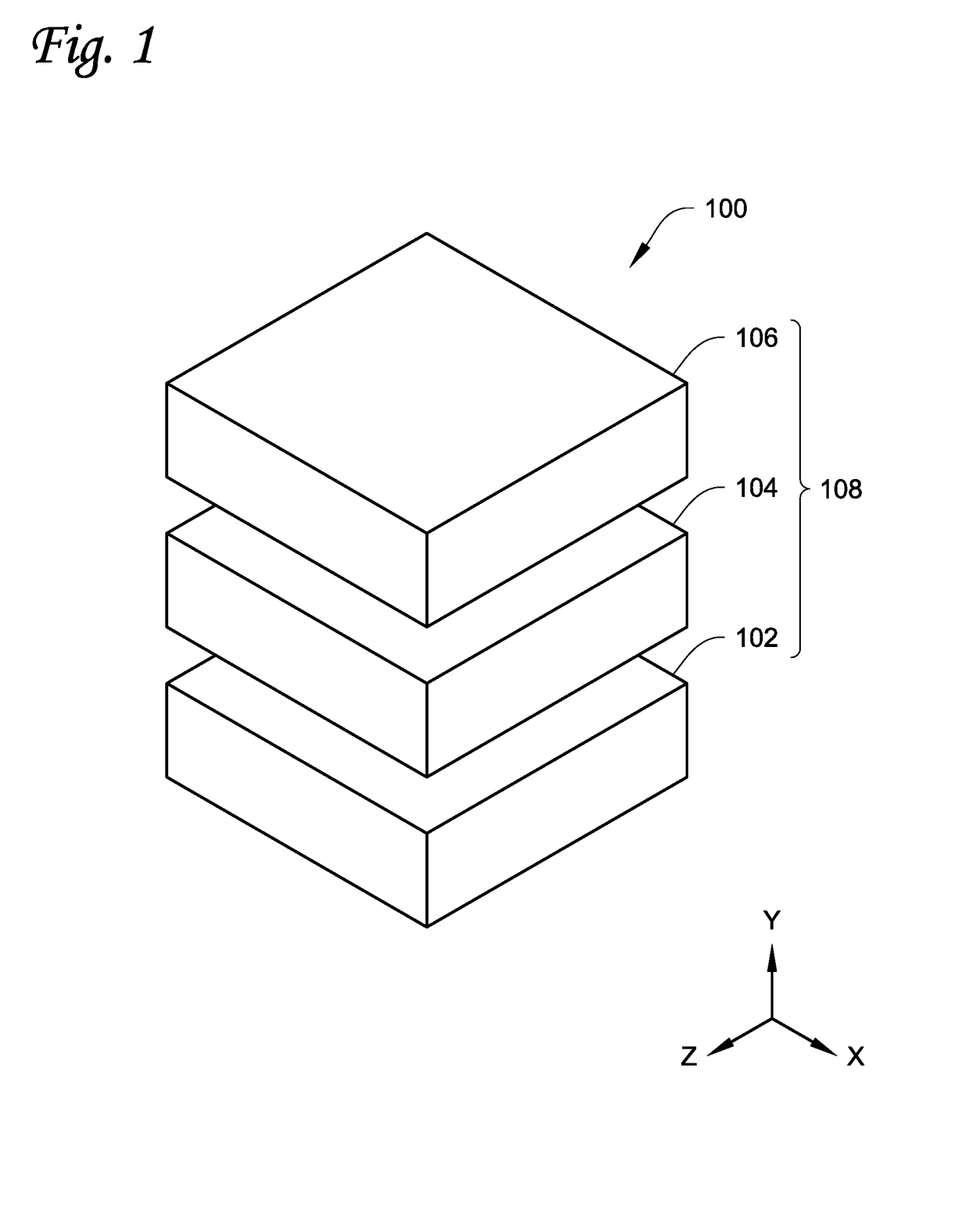
FIG. 1 illustrates a perspective view of a molecular sensing device according to an example of an embodiment.

Referring to the figures, FIG. 1 is a perspective view of a molecular sensing device 100, according to an example of an embodiment. The molecular sensing device 100 includes a plurality of layers 108. In this example, the plurality of layers 108 includes a microfluidics layer 102, a transduction layer 104, and a transceiver layer 106. The layers depicted in FIG. 1 are intended to be illustrative. In some embodiments, the molecular sensing device 100 may include fewer or additional layers. Further information on the construction and operation of a multi-layer molecular sensing device can be found in U.S. Patent Application Publication No. 2013/0018243 the entire contents of which are incorporated herein by reference.

As illustrated in FIG. 1, the plurality of layers 108 are arranged to form a multi-layered structure. In an embodiment, the transduction layer 104 is disposed between the microfluidics layer 102 and the transceiver layer 106 to form the multi-layered structure. Each layer among the plurality of layers 108 is connected to an adjacent layer via a connection. The transduction layer 104 is fluidly connected to the microfluidics layer 102. A fluid connection is a connection between at least two layers in which a fluid sample, such as a gas and/or a liquid, may pass from one layer to the other for analysis. The fluid sample may include solids within the fluid. The transceiver layer 106 is electromechanically connected to the transduction layer 104. The electro-mechanical connection is a connection between at least two layers in which an electrical and/or a mechanical connection is shared between the layers. In some embodiments, the plurality of layers 108 are arranged in the multi-layered structure along a vertical axis Y. The plurality of layers 108 are configured to function together to collect, detect, and communicate the presence of an analyte in the sample.

Each layer among the plurality of layers 108 is configured to perform a particular function. The microfluidics layer 102 is configured to collect a sample from an environment that the sensing device 100 is located in. The environment may be within a human or animal body or within a pipeline or within some other environment one wishes to monitor (collectively referred to as an in vivo or internal environment). The environment may also be on or near a human or animal body, on or near a pipeline, or on or near some other environment one wishes to monitor (collectively referred to as an in vitro or external environment).

The transduction layer 104 is configured to detect a presence of at least one specific analyte within the sample collected by the microfluidics layer 102. In the illustrated example, the transduction layer 104 is disposed between, and can be in intimate contact with, the microfluidics layer 102 and the transceiver layer 106.

The transceiver layer 106 is configured to generate one or more electrical signals in response to the one or more analytes detected by the transduction layer 104 and configured to transmit the electrical signal(s) which is received by an external receiving device, for example a monitoring device. The receiving device can then analyze the received signal(s), for example to determine if a harmful health condition exists.

Figure 2A:
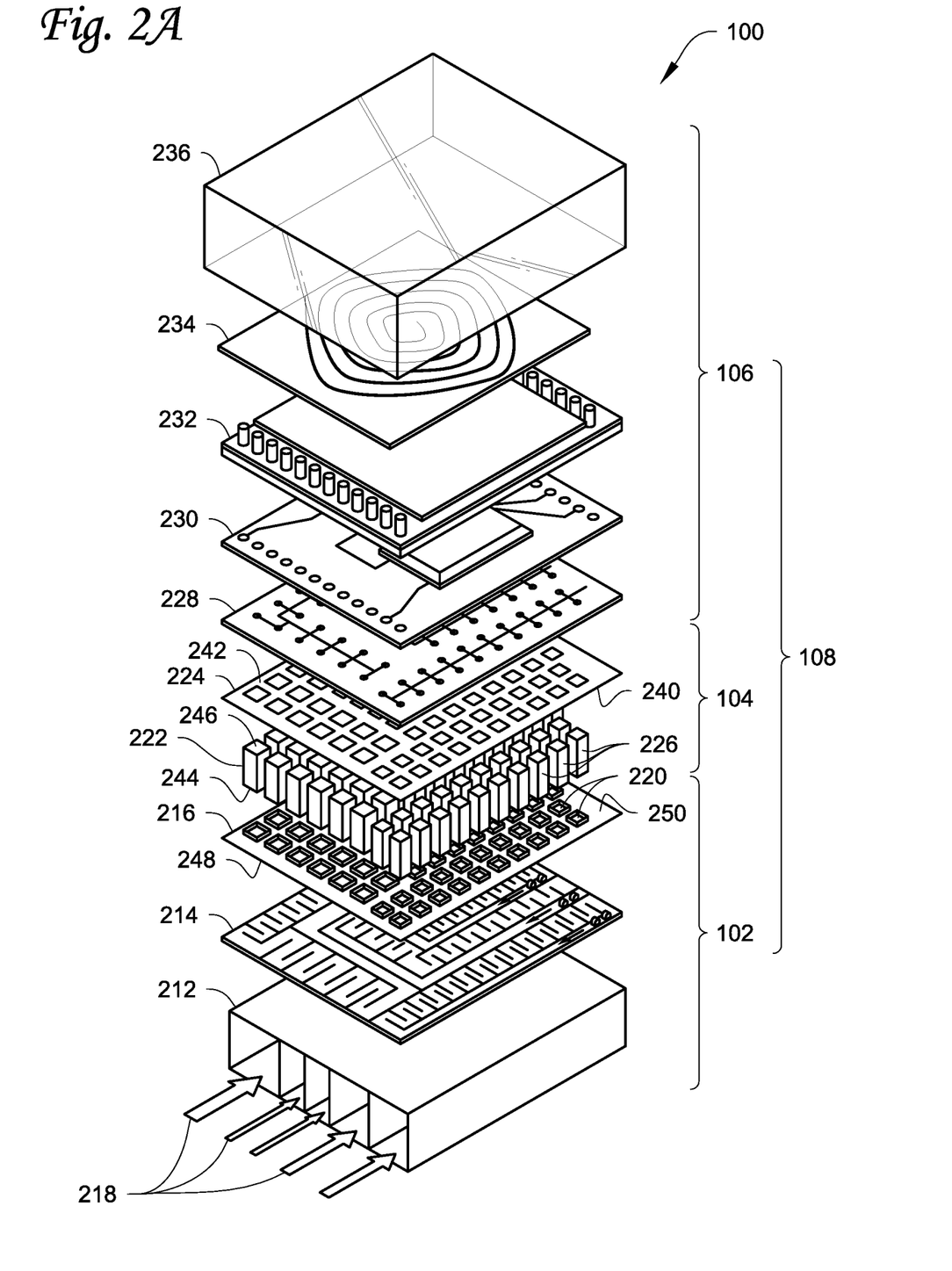
FIG. 2A illustrates an exploded view of the molecular sensing device of FIG. 1.

FIG. 2A illustrates an exploded view of the molecular sensing device 100. The molecular sensing device 100 includes the microfluidics layer 102, the transduction layer 104, and the transceiver layer 106 as previously described in FIG. 1. Each of the layers 102, 104, 106 is further subdivided into a plurality of sub-layers. At least one of the sub-layers of at least one of the layers 102, 104, 106 can be replaced/swapped without replacing/swapping other ones of the sub-layers of the layer 102, 104, 106.

The microfluidics layer 102 includes a filtration sub-layer 212, a capillary sub-layer 214, and a systems sub-layer 216. As illustrated in FIG. 2A, the filtration sub-layer 212 includes input portals 218 that control the collection of test sample material from the environment. When opened, the input portals 218 expose the capillary sub-layer 214, which are microfluidic capillaries that draw-in the test sample from the external environment and pass the sample material through the systems sub-layer 216, which includes a network of micro-electro-mechanical systems (MEMS). The systems sub-layer 216 (e.g., MEMS) filters, separates, and concentrates the sample material through output portals 220 that interface to the transduction layer 104. Further details on the construction and operation of the sub-layers 212, 214, 216 can be found U.S. Patent Application Publication No. 2013/0018243 the entire contents of which are incorporated herein by reference.

The filtration sub-layer 212 includes a number of the input portals 218 which control the collection of one or more samples from the environment. The input portals 218 are filtration tunnels with varying widths, as indicated by varying width of the arrows in FIG. 2A. The filtration tunnels are connected to microfluidic filtration tunnels on a top surface of the filtration sub-layer 212. The filtration tunnels isolate particles of interest from the sample. When an input portal 218 opened, a corresponding microfluidic tunnel is exposed, drawing in the sample from the environment and filters out particles in the sample to be tested. The particles in the sample navigate to the capillary sub-layer 214. The capillary sub-layer 214 collects and concentrates the particles in the sample. The concentrated particles in the sample pass to the systems sub-layer 216, which controls introduction of the particles in the sample to the transduction layer 104 for testing.

Any one of the sub-layers 212, 214, 216 of the microfluidics layer 102 may be replaced without replacing the other sub-layers of the microfluidics layer 102. For example, in some embodiments, the systems sub-layer 216 is replaceable without replacing either the filtration sub-layer 212 or the capillary sub-layer 214, as discussed further herein.

Figure 2B:
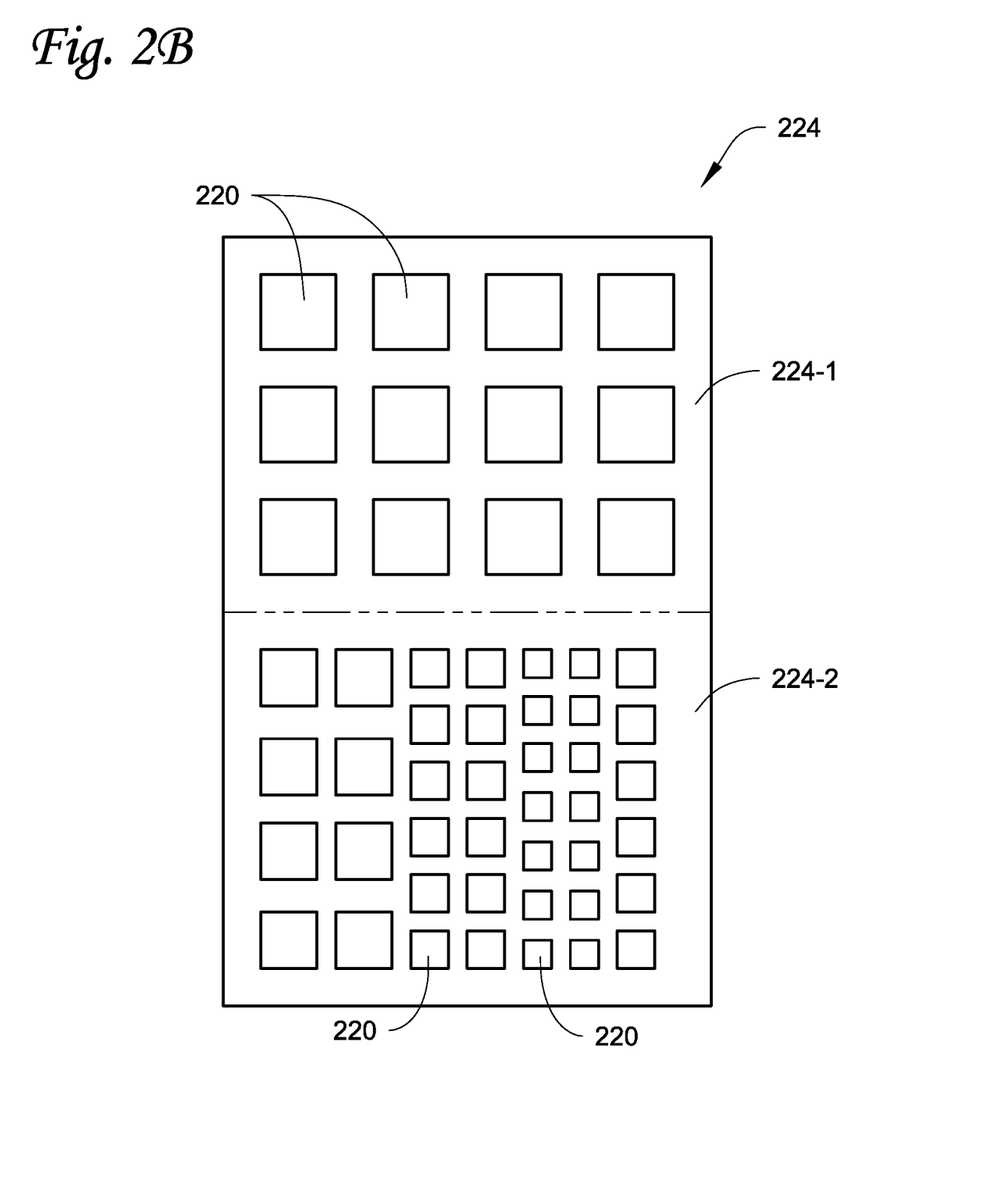
FIG. 2B is a detailed view of the indicated portion of the molecular sensing device in FIG. 2A.

Referring to FIGS. 2A and 2B, the transduction layer 104 includes a well sub-layer 222 and a detector sub-layer 224 that is separate from the well sub-layer 222. The transduction layer 104 detects the biological/chemical signature for a molecular marker in the sample, which is ultimately converted to an electronic signal. The well sub-layer 222 includes a plurality of wells 226 (e.g., tubes) that are configured as a subarray supporting relative measurement capability. The plurality of wells 226 may include different sized wells, same sized wells, and/or a combination of same sized wells and different sized wells. For example, the plurality of wells 226 may have different sized wells having varied lengths and/or widths, which may correspond to the analyte(s) to be detected. The plurality of wells 226 may extend in a vertical direction along the Y-axis within the multi-layered structure. The well sub-layer 222 is exposed to the sample using a small section of the subarray surface for each test cycle. The well sub-layer 222 passes the sample to the detector sub-layer 224 for further analysis.

The detector sub-layer 224 is a highly integrated array of detection elements integrated into tiles, in correspondence with the wells 226, that are configured as subarrays to support relative measurement capability for test cycles. The array of detection elements of the detector sub-layer 224 can be functionalized with different types of surface chemistry. The detector sub-layer 224 can be modified to provide specific surface chemistry to identify targets of interest in the sample. For example, the target analyte can be flowed across the functionalized surface chemistry of the detector sub-layer 224 in which the nanostructure is changed by the surface chemical reaction with the analyte. For instance, DNA, peptides, proteins, or antibodies will react with different molecular markers (i.e., analyte) in the sample. When a molecular marker (i.e., analyte) attaches to a DNA, peptide, protein, or antibody at the detector sub-layer 224, the electric conductivity of the surface changes and emits an electronic signal, which indicates that a particular molecular marker is present in the sample. The detector sub-layer 224 tile surface enables specific subarray clusters with particular surface chemistry to be exposed to the sample. The exposure enables periodic testing of the external or internal environment using only a limited amount of the tile surface for each test cycle. The electronic signal from the transduction layer 104 is processed by the transceiver layer 106, as discussed below.

In some embodiments, at least one of the detector sub-layer 224 or the well sub-layer 222 may be replaceable without replacing the other. In other embodiments, each of the detector sub-layer 224 and the well sub-layer 222 may be replaceable.

The array of detection elements of the detector sub-layer 224 is arranged in a series of rows and columns. Each row and each column can be configured to detect a same or different analyte within the sample by modifying the surface chemistry, as described above. That is, the detector sub-layer 224 can have multi-analyte detection capabilities. For example, a first row may detect a first analyte, a second row may detect a second analyte, a third row may detect a third analyte, and so on. The number of analytes to be detected and the lifespan of the detector sub-layer 224 are inversely related. That is, the fewer the number of analytes to be detected, the longer the lifespan of the detector sub-layer 224 since less of the array is exposed to the sample for testing during each test cycle.

In some embodiments, the detector sub-layer 224 can be a single, continuous stratum. For example, the detector sub-layer 224 can be a single, continuous sheet that is configured to detect a single molecular marker. Alternatively, in some embodiments, the detector sub-layer 224 can be comprised of more than one non-continuous sheet, which may or may not detect different molecular markers. For example, referring to FIG. 2B, a first half 224-1 of the detector sub-layer 224 can be configured with detection elements designed to detect a first molecular marker, while a second half 224-2 of the detector sub-layer 224 can be configured with detection elements designed to detect a second molecular marker.

Referring to FIG. 2A, the transceiver layer 106 includes an amplifier 228, a controller/transceiver 230, a battery 232, and an antenna 234. The amplifier 228 amplifies the electronic signal(s) received from the transduction layer 104. The controller/transceiver 230 receives and processes the amplified electronic signal(s) from the transduction layer 104. In some embodiments, the controller/transceiver 230 can be configured as a computer capable of communicating via a wi-fi network or other network. The battery 232 provides a power source to the controller/transceiver 230. The antenna 234 communicates between the molecular sensing device 100 and other devices such as the external receiving device. In some embodiments, the amplifier 228, the controller/transceiver 230, the battery 232, and the antenna 234 may be referred to as sub-layers of the transceiver layer 106. The transceiver layer 106 is configured to modulate and transmit the electronic signals from the transduction layer 104 to the external receiving device.

A cover 236 is positioned over some or all of the layers 102, 104, 106. The cover 236 includes a top wall and sidewalls, while a bottom-side of the cover 236 is open to receive the multi-layered structure. The cover 236 rests on a top surface of the filtration sub-layer 212 to allow molecules to pass through the input portals 218 in the filtration sub-layer 212.

It will be appreciated that the various sub-layers and components within each layer 102, 104, 106 depicted in FIG. 2A are intended to be illustrative. In some embodiments, the molecular sensing device 100 may include fewer or additional sub-layers, and the sub-layers within each one of the layers 102, 104, 106 may vary. For example, in some embodiments, the transduction layer 104 may include the detector sub-layer 224, the well sub-layer 222, and the amplifier 228. Alternatively, in some embodiments, the transceiver layer 106 may exclude the controller feature of the controller/transceiver 230 while retaining the transceiver feature of the controller/transceiver 230.

One of the sub-layers described herein may be replaced or swapped with a replacement sub-layer. For example, the detector sub-layer 224 may be removed and replaced with another detector sub-layer 224 with a same or different surface chemistry. That is, in some embodiments, at least a portion of the transduction layer 104 and/or at least a portion of the microfluidics layer 102 are configured to be replaceable without replacing a remaining portion of the transduction layer 104 or the microfluidics layer 102. In particular, the detector sub-layer 224, the well sub-layer 222, and/or the systems sub-layer 216 in the molecular sensing device 100 may be removed and/or replaced (i.e., swapped) individually from one another without requiring replacement of other sub-layers.

In some embodiments, the swappable sub-layer can be releasably secured to an adjacent surface. The term "releasably secured" refers to a connection, joining, or an attachment between two surfaces that may be temporary. The swappable sub-layer can be separated from an adjacent surface(s), which allows the swappable sub-layer to be removed from the multi-layered sensing device without removing and/or replacing any other sub-layer or component within the sensing device. Replacing the swappable sub-layer can allow for reuse of the non-removed components, thereby conserving resources and reducing waste. In some embodiments, the swappable sub-layer can be replaced with a different sub-layer that may detect a different molecular marker (e.g., analyte). Non-limiting examples of swappable sub-layers will be discussed in detail below.

The detector sub-layer 224: The detector sub-layer 224 is disposed between the well sub-layer 222 and the amplifier 228. The detector sub-layer 224 includes a first surface 240 (e.g., a lower/bottom surface) and a second surface 242 (e.g., upper/top surface) opposite the first surface 240. In some embodiments, the first surface 240 can be releasably secured, for example using an adhesive, to a surface of a first sub-layer (e.g., the well sub-layer 222) adjacent to the detector sub-layer 224. The adhesive may be formed of a polymer material. For example, the detector sub-layer 224 may include an adhesive on the first surface 240 thereof that joins the detector sub-layer 224 to the well sub-layer 222. The adhesive bond between the respective surfaces can be severed, for example by peeling, to remove the detector sub-layer 224 from the well sub-layer 222. The second surface 242 of the detector sub-layer 224 may be releasably secured, for example using a releasable mechanical connection or using an adhesive, to the amplifier 228 to remove the detector sub-layer 224 from the amplifier 228.

The detector sub-layer 224 may be replaceable in the molecular sensing device 100 without replacing other components. The detector sub-layer 224 may be replaced with a similar or same detector sub-layer. Alternatively, the detector sub-layer 224 may be replaced with a different detector sub-layer having a different surface chemistry to detect a different analyte that may be of interest. For example, the molecular sensing device 100 may initially be used to detect a chemical leak (contamination) related to an environmental concern related to water. The environmental concern may change to require monitoring/detection of a different chemical gas leak (contamination) related to air. In this scenario, the detector sub-layer 224 within the molecular sensing device 100 may be replaced (i.e., swapped) with a different detector sub-layer 224 to detect the molecular marker (i.e., analyte) that pertains to each scenario, while reusing the remaining components of the device 100. The swappable feature of the detector sub-layer 224 enables multiple analyte detection, which may save time to address abatement or health issues related to the detection. Additionally, reuse of the remaining portions of the molecular sensing device 100 may reduce waste and increases an overall lifespan of the device 100.

The well sub-layer 222: The well sub-layer 222 includes a first surface 244 (e.g., a lower/bottom surface) and a second surface 246 (e.g., upper/top surface) opposite the first surface 244. In some embodiments, the first surface 244 can be releasably secured to a surface of a first sub-layer (e.g., the systems sub-layer 216) adjacent to the first surface 244 of the well sub-layer 222, and the second surface 246 can be releasably secured to a surface of a second sub-layer (e.g., the detector sub-layer 224) adjacent to the second surface 246 of the well sub-layer 222. For example, the well sub-layer 222 may include adhesive on the first surface 244 (e.g., lower/bottom surface) and on the second surface 246 (e.g., upper/top surface). The adhesive between the respective surfaces can be broken, for example by peeling, to remove the well sub-layer 222 from the molecular sensing device 100 to replace the well sub-layer 222. Removing and replacing the well sub-layer 222 can include similar benefits as removing and replacing the detector sub-layer 224 discussed above.

The systems sub-layer 216: The systems sub-layer 216 includes a first surface 248 (e.g., a lower/bottom surface) and a second surface 250 (e.g., upper/top surface) opposite the first surface 248. In some embodiments, the first surface 248 can be releasably secured to a surface of a first sub-layer (e.g., the capillary sub-layer 214) adjacent to the first surface 248 of the systems sub-layer 216, and the second surface 250 can be releasably secured to a surface of a second sub-layer (e.g., the well sub-layer 222) adjacent to second surface 250 of the systems sub-layer 216. The releasable connections can be achieved using, for example, adhesive and/or mechanical connections as described above for the sub-layers 22, 224. Removing and replacing the systems sub-layer 216 can clear any clogged channels within the MEMS, which can enable the sample to flow to the transduction layer 104 for analysis.

Any combinations of the detector sub-layer 224, the well sub-layer 222, and the systems sub-layer 216 can be removed and replaced. In some embodiments, the detector sub-layer 224 and the well sub-layer 222 can both be removed and replaced, collectively together (i.e. at the same time as a single unit) or separately and individually. The first surface 244 of the well sub-layer 222 can be releasably secured to a first layer (e.g., the microfluidics layer 102), while the second surface 242 of the detector sub-layer 224 can be releasably secured to a second layer (e.g., the transceiver layer 106).

Alternatively, in some embodiments, all three of the sub-layers 222, 224, 216 can be removed and replaced, collectively together (i.e. at the same time as a single unit) or separately and individually, in which case the first surface 248 of the systems sub-layer 216 can be releasably secured to a first sub-layer (e.g., the capillary sub-layer 214), while the second surface 242 of the detector sub-layer 224 can be releasably secured to a second layer (e.g., the transceiver layer 106). Additionally, or alternatively, the systems sub-layer 216 may be releasably secured via an adhesive and/or peeled from the second layer (e.g., the transceiver layer 106).

Figure 3:
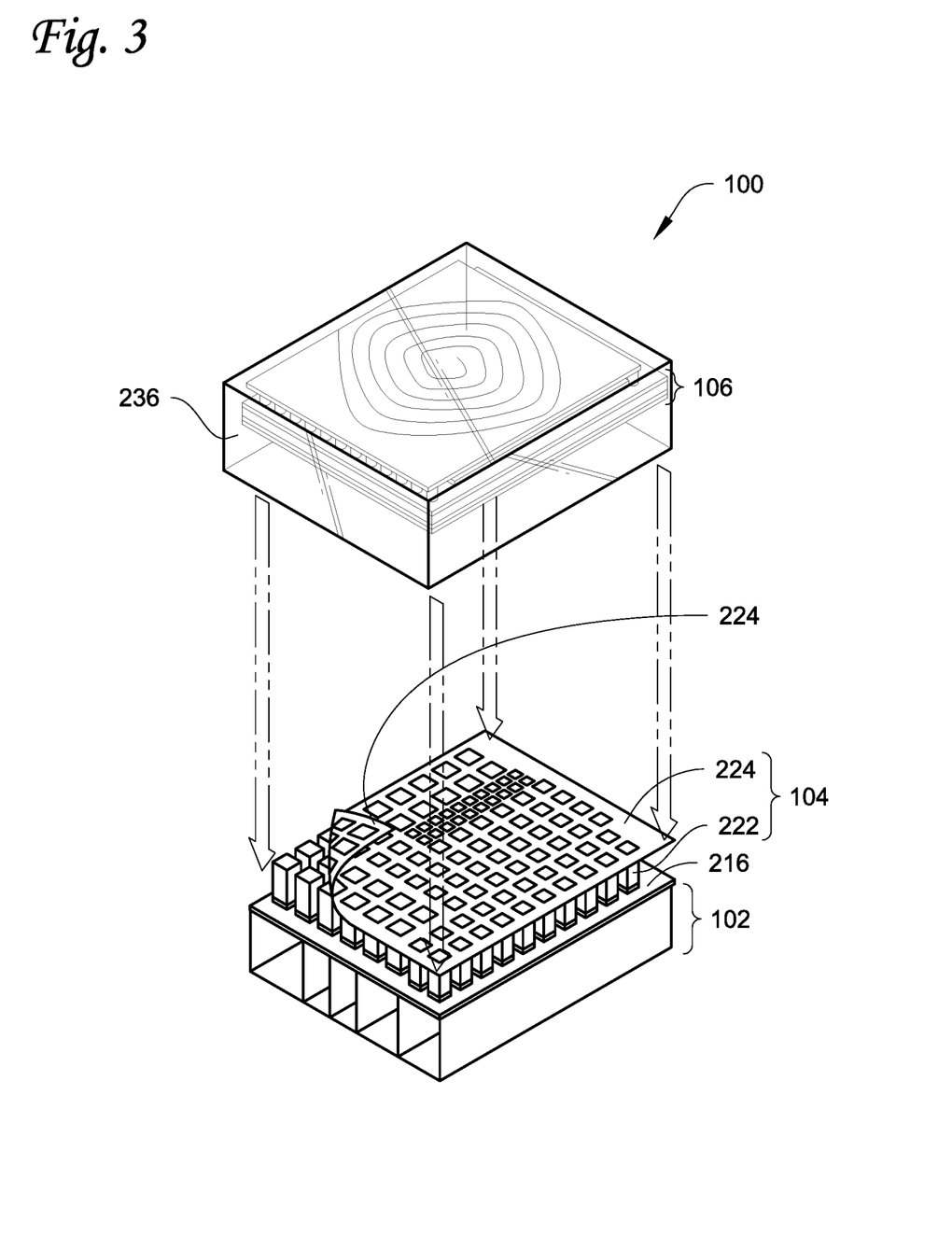
FIG. 3 illustrates a partially exploded view of the molecular sensing device of FIG. 2A.

FIG. 3 illustrates a partially exploded view of the molecular sensing device 100 showing peeling of one of the sub-layers, in this example the detector sub-layer 224, from the device 100. As used herein, "peelable" refers to removal of a sub-layer layer from the molecular sensing device 100 by means of pulling or stripping the sub-layer which is adhered to another surface. As illustrated in FIG. 3, a portion of the detector sub-layer 224 is peeled or pulled away from the surface below. The well sub-layer 222 and the systems sub-layer 216 may be peeled from their adjoining surfaces in a similar manner.

The entire sub-layer may be removed, or only a portion of the sub-layer may be removed. Therefore, the language "remove the sub-layer" or the like as used herein includes removal of the entire sub-layer as well as removal of only a portion of the sub-layer.

In FIG. 3, the detector sub-layer 224 is between the transceiver layer 106 and the well sub-layer 222, and the detector sub-layer 224 is removably secured to the transceiver layer 106 and to the well sub-layer 222. In particular, the first surface 240 of the detector sub-layer 224 can be releasably secured to the second surface 246 of the well sub-layer 222 via an adhesive. The adhesive may be formed of a polymer material. The adhesive permits removal of the detector sub-layer 224 by peeling the detector sub-layer 224 from the well sub-layer 222. The peeling of the detector sub-layer 224 can occur after the detector sub-layer 224 is detached from the amplifier 228, for example by loosening the electro-mechanical connection between the two.

In some embodiments, the swappable sub-layer may be peelable from between two adjacent surfaces. That is, both surfaces (e.g., top surface and bottom surface) of a respective sub-layer may be peelable. For example, in some embodiments, the well sub-layer 222 is disposed between the systems sub-layer 216 and the detector sub-layer 224. The first surface 244 of the well sub-layer 222 can be releasably secured to the surface of the systems sub-layer 216 via an adhesive, and the second surface 246 of the well sub-layer 222 can be releasably secured to the surface of the detector sub-layer 224 via an adhesive. The well sub-layer 222 may then be peelable from each of the systems sub-layer 216 and the detector sub-layer 224.

In one embodiment, the molecular sensing device 100 can be reconfigured by removing at least a portion of the transduction layer 104 (such as one or both of the sub-layers 222, 224) and/or at least a portion of the microfluidics layer 102 (such as the systems sub-layer 216) without removing a remaining portion of the transduction layer 104 or the microfluidics layer 102. The removed sub-layer can then be replaced with a replacement sub-layer portion having a similar configuration and/or functionality or replaced with a replacement sub-layer portion having a different configuration and/or functionality.

The examples disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. A sensor, comprising:
 a microfluidics layer, the microfluidics layer is configured to collect a sample from an environment;
 a transduction layer fluidly connected to the microfluidics layer, the transduction layer is configured to detect a presence of an analyte within the sample, wherein the transduction layer includes a detector sub-layer and a well sub-layer that includes a plurality of wells, and at least one of the detector sub-layer or the well sub-layer are replaceable, wherein the detector sub-layer includes a first surface and a second surface opposite the first surface, and the first surface is releasably secured to a surface of a first sub-layer adjacent to the detector sub-layer;
 a transceiver layer electro-mechanically connected to the transduction layer, the transceiver layer is configured to generate an electrical signal in response to the analyte detected by the transduction layer and configured to transmit the electrical signal; and
 wherein at least a portion of the transduction layer and/or at least a portion of the microfluidics layer is configured to be replaceable without replacing a remaining portion of the transduction layer or the microfluidics layer.

2. The sensor in claim 1, wherein the transduction layer is disposed between the microfluidics layer and the transceiver layer to form a multi-layered structure.

3. The sensor of claim 1, wherein each of the detector sub-layer and the well sub-layer are replaceable.

4. The sensor of claim 1, wherein the microfluidics layer includes a systems sub-layer that includes a plurality of micro-electro-mechanical systems (MEMS), and the systems sub-layer is replaceable.

5. The sensor of claim 1, wherein the first surface is releasably secured to the surface of the first sub-layer via an adhesive, whereby the detector sub-layer is peelable from the first sub-layer.

6. The sensor of claim 1, wherein the second surface is releasably secured to a surface of a second sub-layer adjacent to the well sub-layer.

7. The sensor of claim 6, wherein the first surface is releasably secured to the surface of the first sub-layer via an adhesive, and the second surface is releasably secured to the surface of the second sub-layer via an adhesive, whereby the well sub-layer is peelable from each of the first and second sub-layers.

8. The sensor of claim 1, wherein:
 the well sub-layer includes a first surface and a second surface opposite the first surface; the first surface of the detector sub-layer faces and is adjacent to the second surface of the well sub-layer;
 the first surface of the detector sub-layer is releasably secured to the second surface of the well sub-layer; and
 the first surface of the well sub-layer is releasably secured to a surface of a first sub-layer adjacent to the well sub-layer.

9. The sensor of claim 8, wherein the first surface of the detector sub-layer is releasably secured to the second surface of the well sub-layer via an adhesive whereby the detector sub-layer is peelable from well sub-layer; and the first surface of the well sub-layer is releasably secured to the surface of the first sub-layer via an adhesive whereby the well sub-layer is peelable from the first sub-layer.

10. A molecular sensor, comprising:
 a microfluidics layer, the microfluidics layer is configured to collect a sample from an environment;
 a transduction layer fluidly connected to the microfluidics layer, the transduction layer includes a detector sub-layer that is configured to detect a presence of an analyte within the sample, and a well sub-layer that includes a plurality of wells; and a transceiver layer electro-mechanically connected to the transduction layer, the transceiver layer is configured to generate an electrical signal in response to the analyte detected by the transduction layer and configured to transmit the electrical signal;

wherein the microfluidics layer, the transduction layer, and the transceiver layer form a multi-layered structure; and wherein the detector sub-layer is between the transceiver layer and the well sub-layer, and the detector sub-layer is removably secured to the transceiver layer and to the well sub-layer.

11. The sensor of claim 10, wherein at least one of the detector sub-layer or the well sub-layer are individually replaceable.

12. The sensor of claim 10, wherein the microfluidics layer includes a systems sub-layer that includes a plurality of micro-electro-mechanical systems (MEMS), and the systems sub-layer is replaceable.

13. A method of reconfiguring a molecular sensor having a transduction layer between a microfluidics layer and a transceiver layer, wherein the transduction layer includes a detector sub-layer and a well sub-layer that includes a plurality of wells, and at least one of the detector sub-layer or the well sub-layer are replaceable, wherein the detector sub-layer includes a first surface and a second surface opposite the first surface, and the first surface is releasably secured to a surface of a first sub-layer adjacent to the detector sub-layer, the method comprising:

removing at least a portion of the transduction layer and/or at least a portion of the microfluidics layer without removing a remaining portion of the transduction layer or the microfluidics layer, wherein removing at least the portion of the transduction layer and/or at least the portion of the microfluidics layer comprises peeling the first surface from the surface of the first sub-layer adjacent to the detector sub-layer; and replacing the removed portion with a replacement portion.

14. The method of claim 13, wherein removing at least the portion of the transduction layer and/or at least the portion of the microfluidics layer comprises peeling the detector sub-layer from the well sub-layer.

15. The method of claim 13, wherein removing at least the portion of the transduction layer and/or at least the portion of the microfluidics layer comprises peeling the well sub-layer from the detector sub-layer.

16. The method of claim 13, wherein:
the microfluidics layer includes a systems sub-layer that includes a plurality of micro-electro-mechanical systems (MEMS); and
the method further comprises peeling the systems sub-layer from the transduction layer.

17. The method of claim 13, wherein the replacement portion has a different functionality than the removed portion.

18. The molecular sensor of claim 10, wherein the detector sub-layer includes a first surface and a second surface opposite the first surface, and the first surface is releasably secured to a surface of a first sub-layer adjacent to the detector sub-layer.

19. The molecular sensor of claim 18, wherein the first surface is releasably secured to the surface of the first sub-layer via an adhesive, whereby the detector sub-layer is peelable from the first sub-layer.

20. The molecular sensor of claim 18, wherein the well sub-layer includes a first surface and a second surface opposite the first surface, the first surface is releasably secured to a surface of a first sub-layer adjacent to the well sub-layer, and the second surface is releasably secured to a surface of a second sub-layer adjacent to the well sub-layer.

* * * * *